United States Patent [19]

Hellekant et al.

[11] Patent Number: 5,527,555
[45] Date of Patent: *Jun. 18, 1996

[54] BRAZZEIN SWEETENER

[75] Inventors: Bengt G. Hellekant; Ding Ming, both of Madison, Wis.

[73] Assignee: Wisconsin Alumni Research Foundation, Madison, Wis.

[ * ] Notice: The term of this patent shall not extend beyond the expiration date of Pat. No. 5,326,580.

[21] Appl. No.: 242,655

[22] Filed: May 13, 1994

Related U.S. Application Data

[60] Continuation-in-part of Ser. No. 84,846, Jun. 29, 1993, Pat. No. 5,346,998, which is a division of Ser. No. 21,540, Feb. 16, 1993, Pat. No. 5,326,580.

[51] Int. Cl.$^6$ ............... A23L 1/236; C12N 15/29; C07K 14/415
[52] U.S. Cl. ............... 426/548; 536/23.6; 530/324; 435/69.1
[58] Field of Search ............... 530/324, 379; 426/548; 435/69.1; 536/23.6

[56] References Cited

U.S. PATENT DOCUMENTS 5,326,580  7/1994  Hellekant et al. ............... 426/548
5,346,998  9/1994  Hellekant et al. ............... 536/23.6

FOREIGN PATENT DOCUMENTS

0502474A2  9/1992  European Pat. Off. .

WO94/19467  9/1994  WIPO .

OTHER PUBLICATIONS

Ming, et al., "Brazzein, a natural thermostable sweet protein from *Pantadiplandra brazzeana*," Chemical Senses; Fifteenth Annual Meeting of the Association for Chemoreception Sciences, Sarasota, Florida, U.S.A., 18(5):601, 1993.

Ming, et al., "Chemical modification of Brazzein, a sweet protein from *Pentadiplandra brazzeana*," Sixteenth Annual Meeting of the Association for Chemoreception Sceinces, Sarasota, Florida, U.S.A., 19(5):521, 1994.

Yamashita, et al., "Purification and Complete Amino Acid Sequence of a New Type of Sweet Protein with Taste–modifying Activity, Curculin," *J. Biolog. Chem.* 265:15770–15775, 1990.

van der Wel, et al., "Isolation and characterization of pentadin the sweet principle of *Pentadiplandra–brazzeana* baillon," *Chem. Sen.* 14(1):75–80, 1989.

*Primary Examiner*—Robert A. Wax
*Assistant Examiner*—G. E. Bugaisky
*Attorney, Agent, or Firm*—Quarles & Brady

[57] ABSTRACT

Disclosed herein is a protein sweetener that has been isolated from *Pentadiplandra brazzeana* Baillon. The sweetener is thermostable, lysine rich, and has a relative lasting taste. Also disclosed is a recombinant host capable of producing the sweetener in large quantities. Compositions of this sweetener with other sweeteners are also disclosed.

5 Claims, 2 Drawing Sheets

BRAZZEIN SWEETENER

RELATED APPLICATIONS

This application is a continuation-in-part U.S. Ser. No. 08/084,846, filed Jun. 29, 1993, now U.S. Pat. No. 5,346,998, which in turn is a divisional of U.S. Ser. No. 08/021,540, U.S. Pat. No. 5,326,580, filed Feb. 16, 1993.

FIELD OF THE INVENTION

The present invention relates to the identification and isolation of a sweet protein from the plant *Pentadiplandra brazzeana* Baillon. It also relates to the sequencing of that protein and the creation of a DNA sequence capable of producing the protein artificially.

BACKGROUND OF THE INVENTION

The most widely used natural sweetener, sugar, has problems associated with its use (especially causing weight gain by users). Many other sweeteners either have undesirable side effects or are deficient in certain respects. For example, aspartame loses its sweetness when exposed to elevated temperatures for long periods. This renders aspartame unsuitable for use in most baking applications.

Another problem is that existing artificial sweeteners have temporal sweetness profiles which do not exactly match that of sugar. For example, the sweetness may die out sooner. It may therefore be desirable to mix an existing artificial sweetener with another sweetener having a different temporal profile (so as to create a mixed sweetener that more closely matches the overall temporal sweetness profile of sugar).

Thus far, only relatively few sweet proteins (as distinguished from sweet carbohydrates) have been found in nature. See e.g. J. A. Morris et al., Biochem. Biophys. Acta. 261:114–122 (1972) (Monellin); H. Van Der Wel, FEBS Letters 21(1):88–90 (1972) (Thautmatin); D. Ming et al., Acta Botanica Yunnanica 8(2):181–192 (1986) (Mabinlin); and H. Yamashita et al., J. Bio. Chem. 265 (26):15770–15775 (1990) (Curculin). The disclosure of these articles and of all other articles referred to herein are incorporated by reference as if fully set forth herein. These sweet proteins are many times sweeter (for a given weight) than sugar, and are lower in calories.

The search for non-carbohydrate sweeteners has led to an examination of various plants which are known to be sweet. In H. van der Wel, et al., 14 Chemical Senses 75–79 (1989) the authors reported the existence of a sweet protein in *Pentadiplandra brazzeana* Baillon of about 12,000 Daltons per subunit that they named "Pentadin". This plant is a climbing shrub found in tropical Africa, especially in Gabon. It bears red globular berries of approximately five centimeters in diameter. Under their thick epicarp, these berries contain one to five reniform seeds surrounded by a thick soft layer of red pulp. The fruit used by these authors in their isolation attempt was a smoked and dried form of the plant. Unfortunately, attempts to isolate purer forms of Pentadin were unsuccessful.

As such, it can be seen that the need exists for an improved low calorie sweetener, especially one that is heat stable and has a different temporal sweetness profile from known artificial sweeteners.

SUMMARY OF THE INVENTION

One aspect of the present invention provides the protein "Brazzein" in a form that is essentially free of other *Pentadiplandra brazzeana* Baillon plant material besides Brazzein. Brazzein is a second, previously unknown, sweet protein isolated from this plant.

In another aspect, the invention provides a composition of Brazzein mixed with another sweetener. Preferably, the other sweetener has a sweetness temporal profile which provides a faster sweetness response than Brazzein.

In another aspect, the invention provides a recombinant host that contains a nucleotide sequence coding for the protein Brazzein.

The invention involves the isolation of a new sweet protein from *Pentadiplandra brazzeana* Baillon, herein named "Brazzein". The protein is about 6,473 Daltons in size and is about 2,000 times sweeter in 2% solution than a 2% sucrose solution. Thermostability tests indicate that this protein has greatly desired heat stability characteristics (thus making it much more suitable for use in connection with baking). In this regard, the protein still tasted very sweet after two hours of incubation at 98° C.

Moreover, Brazzein elicited a relatively long lasting sweetness response. Thus, Brazzein is especially suitable to being mixed with other known artificial sweeteners (e.g. acesulfameK) that elicit a quick, but short sweetness response.

A sample of Brazzein has been sequenced and an amino acid sequence therefore is SEQ ID NO:4. A DNA sequence coding for that sample of Brazzein is listed at SEQ ID NO:5. A DNA sequence coding for that sample of Brazzein which is specially designed for use in an *E. coli* expression system host is provided at SEQ ID NO:6. It will be appreciated that various other nucleotide sequences coding Brazzein can be developed using conventional techniques based on the SEQ ID NO:5 sequence provided herein. In this regard, for many expression systems there are optimal codons for each amino acid. To optimize Brazzein production in another specific host, one would create a nucleotide sequence encoding Brazzein that incorporated these preferred, optimal codons.

The protein of the present invention should also be useful as a flavor enhancer (apart from its sweetness). Further, when mixed with enzymes it is expected to increase their overall thermostability.

Also, the DNA sequence of the present invention should be suitable to be inserted into hosts other than bacteria. For example, if the DNA were expressed in transgenic tomato or carrot plants (using what are now well known techniques), a sweet plant would result. See generally M. Chilton, 248 Scientific American 50–59 (1983) (carrot). Similarly, animals could have their genes modified so that foods derived from them would be sweeter. See B. Wang et al., 51 Cancer Res. 2642–2648 (1981) (genes in bovine mammary epithelial cells—modified milk).

It is an object of the invention to provide a protein sweetener that is stable when exposed for long periods of time to elevated temperatures.

It is another object to provide a sweetener which has a temporal profile which involves a slow but sustained sweetness response.

It is yet another object of the invention to provide Brazzein in large quantities, at low cost, by artificial means.

It is yet another object of the invention to provide a gene coding for Brazzein.

Still other objects and advantages of the present invention will become apparent from the following description. It should be appreciated that what follows is merely the preferred embodiments of the invention. Various other embodiments of the invention are also intended to be within the scope of the claims. Thus, the preferred embodiments should be understood merely as examples of the present invention.

DESCRIPTION OF THE PREFERRED EMBODIMENTS

Materials

Our initial source for Brazzein is the fruit of *Pentadiplandra brazzeana*, a species described as a Tiliacae by Baillon in 1868, and which is presently classified in the Pentadiplandraceae, a family created by Hutchinson. See. J. Hutchinson, Pentadiplandraceae, In Hutchinson, J. and Dalziel, J. M. (eds)., *Flora of West Tropical Africa* I.461 (1928).

Under its nutshell-like epicarp, the berries of this plant contain three to five reniform seeds surrounded by a thick soft layer of pulp, which turns from green to red during ripening. Brazzein is distributed in the pulp from epicarp to seed and the content of Brazzein in the ripe fruit appears to be roughly 0.2% to 0.05% by weight.

The chemicals we used in our experiment were mostly from Sigma Chemical Co., St. Louis, Mo. The organic solvents such as acetonitrile, trifluoroacetic acid, 4-vinylpyridine, methanol, ethanol, etc. were from Aldrich; Liquid chromatography equipment was from Pharmacia, Pharmacia LKB Biotechnology, Piscataway, N.J.; HPLC system was from Waters, Millipore Corp., Bedford, Mass.; Ultrafiltration equipment was from Amico Corp., Danvers, Mass.; and the electrophoresis equipment was from Pharmacia LKB Biotechnology, and Novex Experimental Technology, San Diego, Calif.

Brazzein Purification

Protein Extraction

The soft pulp was separated from the epicarp and seeds and the pulp was extracted with extracting buffer (1:40 w/v) containing 0.05M sodium acetate, pH 5.0; 0.1 mM dithiothreitol; 5% glycerol; and 0.5% PVP for 30 min. We then filtered the extracting solution using Whatman filter paper #54. The obtained filtrate was centrifuged at 10,000×g for 20 min and the supernatant (containing the protein of interest) was saved.

Salt Precipitation

Solid ammonium sulfate was added to the supernatant to 30% saturation. We also added a drop of 1M sodium hydroxide per 10 grams of ammonium sulfate added. After this we store the solution on ice for 30 min. At this point we centrifuged the solution and discarded the precipitate.

We then added solid ammonium sulfate to the supernatant to 90% saturation, and stored the container at 4° C. overnight. An additional precipitate was then-collected by centrifugation at 10,000×g for 40 min. This time the precipitate was kept.

Gel Filtration

Figure 1:
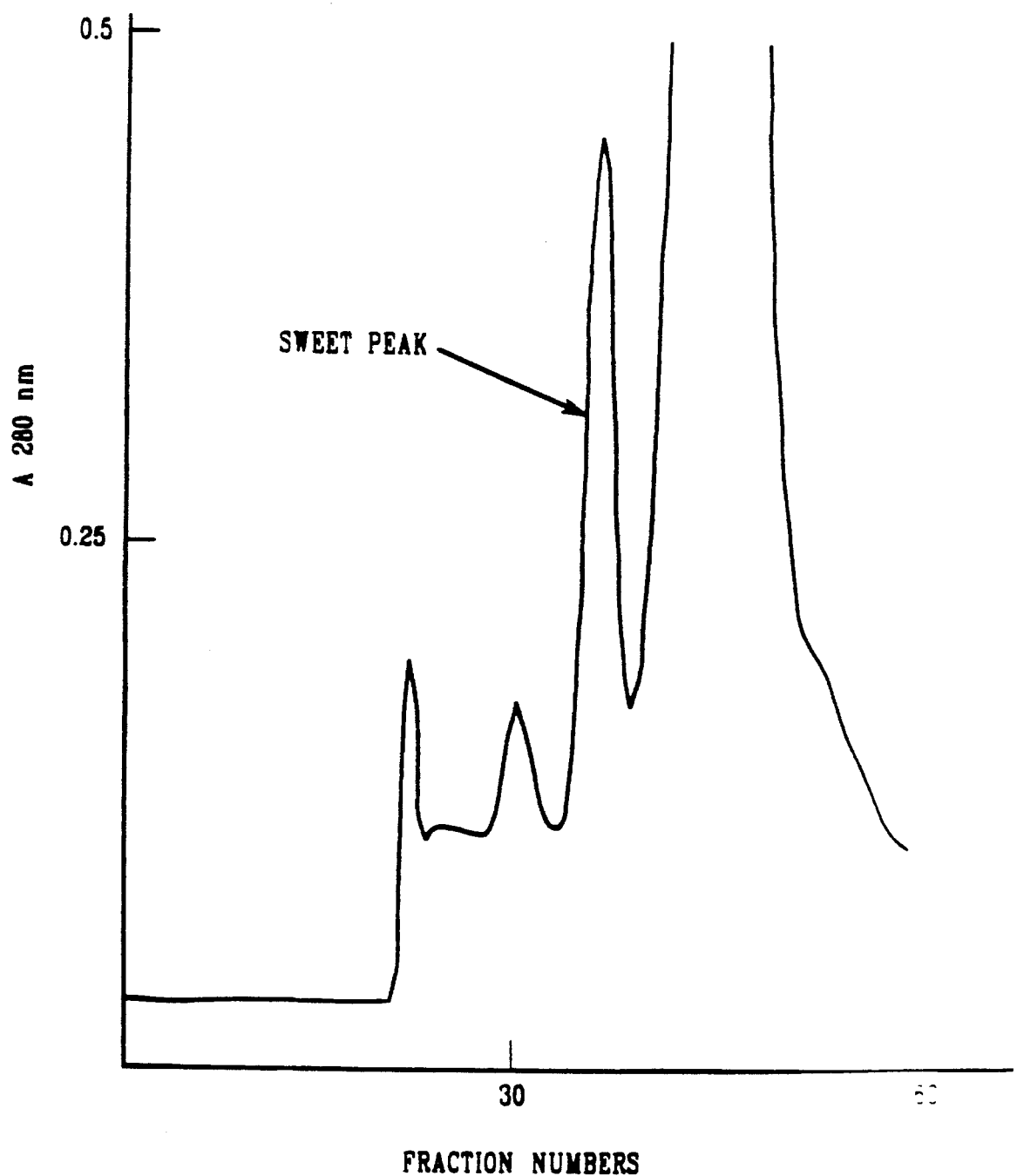
FIG. 1 shows a gel filtration chromatography graph.

A Sephadex G-75 (Pharmacia) column (2.0 cm×80 cm) was pre-equilibrated with 0.5M NaCl; 0.02M NaAc, pH 5.0. This solution was also used as the elution buffer. The second precipitate from the above procedure was dissolved in 0.5M NaCl in 0.02M NaAc, pH 5.0. Seven ml of the sample solution was loaded on for each run and the flow rate was controlled at ~0.5 ml per min. Fractions were collected and screened for sweetness by tasting. Fractions 35–43 were found to be sweet and were therefore pooled for further purification. FIG. 1 is a chart of the Sephadex column fractions versus absorbance at 280 nm.

When used as a way to estimate the molecular weight of the protein, a G-75 Sephadex column (1.5×100 cm) was set up as above, but the flow rate was slowed down to half of the value above. We used Albumin (BSA, 66,000), Carbonic Anhydrase (CA, 29,000), Cytochrome C (CytC, 12,400) and Aprotinin (APR, 6,500) as the molecular weight standards.

Cation Exchange Chromatography

Figure 2:
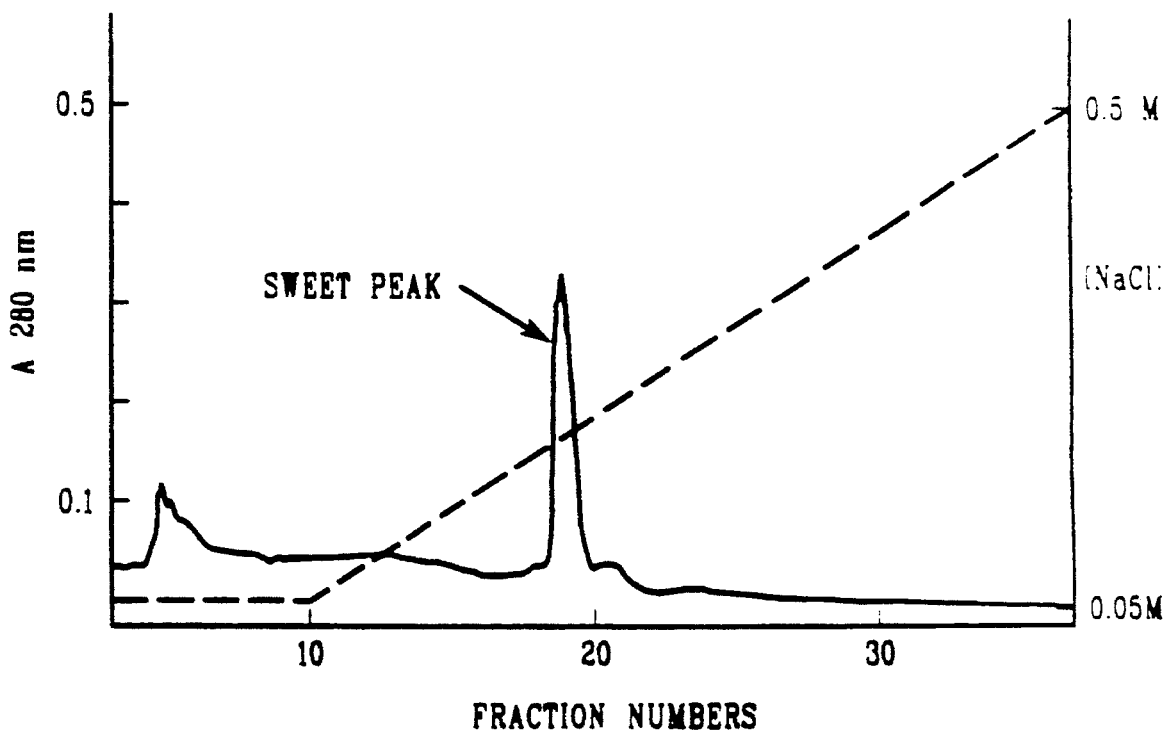
FIG. 2 shows a cation exchange chromatography graph.

A CM-Cellulose CM 52 (Whatman) column (2.5 cm×40 cm) was pre-balanced with 0.02M NaAc, pH 5.0 overnight. The pooled sample (fractions 35–43) from the Sephadex gel filtration was diluted with double distilled water five fold and then loaded on the column directly. We then eluted the protein with a linear gradient of NaCl generated by Gradient Mixer GM-1 (Pharmacia) from 0.05M to 0.5M. Fractions comprising the major peak, as detected by absorbance at 280 nm, were pooled and tasted to confirm that the major peak was sweet. FIG. 2 is a diagram of the column fractions versus absorbance at 280 nm.

Anion Exchange Chromatography

A DEAE-Cellulose column was equilibrated with 0.05M Tris-HCl (pH 8.5). The major peak fraction from the cation exchange column was concentrated and desalted by ultrafiltration with an Amico 8400 ultrafiltration unit with a YM3 membrane. The concentrated and desalted sample was loaded on the anion exchange column. The peak ("Brazzein") was eluted with 0.1M NaCl in 0.05M Tris-HCl.

Preparative Reverse Phase HPLC

As an alternative to the anion exchange chromatography step, a $C_4$-DYNAMAX RP column (4.6×250 mm) can be used in further purification. Elutant A is 0.1% Trifluoroacetic acid (TFA) and elutant B is 80% acetonitrile in 0.086% TFA. Linear gradient elution was used here and flow rate was controlled at 1 ml/min.

Cysteine Alkylation

To study Brazzein conformation, the protein's cysteines can be alkylated. Alkylation with 4-vinylpyridine (see C. S. Fullmer, Anal. Biochem. 142, 336–339 (1984)) can be done in 0.5M N-ethylmorpholine, pH 8.3 with 6M Guanidinium HCl. The protein is reduced with 25 mM DTT first for four hours, then 8 ul 4-VP can be added per 100 nmole protein and incubated under room temperature overnight.

In the alternative, one can alkylate with iodoacetamide. The reaction will be similar except that 8M urea was used instead of 6M Guanidinium HCl.

When alkylated Brazzein was electrophoresed, no subunit aggregation was observed. This phenomenom strongly suggests that aggregation happens through disulfide bonds.

Sodium Dodecyl Sulfate Polyacrylamide Gel Electrophoresis (SDS-PAGE)

To further characterize the protein's molecular weight and its relative purity or abundance, a modified Tricine-SDS-PAGE system (see H. Schägger et al., Anal. Biochem. 166:368–379 (1987)) was used in a Novex precasted gel cassette. The composition of the separation gel, the spacer gel, and the stacking gel was 16.5%T, 3%C, 10%T, 3%C, and 4%T, 3%C. "T" is the weight percentage of total monomer (acrylamide plus cross-linker, in grams per 100 ml) and "C" is the proportion of cross-linker as a percentage of total monomer in the gel. The molecular weight was calculated according to 3 groups of molecular weight standards. Generally, the alkylated or unalkylated protein samples were treated for about 30 min at 50° C. in 4% SDS, 12% glycerol (w/v), 50 mM Tris, 0.01% Bromophenol Blue adjusted with HCl to pH 6.8 with or without 2% mercaptoethanol (v/v) depending on the circumstances. The electrophoresis was carried out under the condition of 5 V/cm. When electrophoresis is completed, the gel was stained in Comassie Brilliant Blue R-250 staining Solution A (30 mg dye in 1 L of fixative solution of 65% water, 25% isopropanol and 10% acetic acid) for 15 min, and then changed to Solution B (30 mg dye in 1 L of staining solution of 80% water, 10% isopropanol and 10% acetic acid). The gel was left in Solution B overnight. The molecular weight was estimated at a value very close to the theoretical molecular weight of SEQ ID NO:1.

UV Absorption Spectrum

The UV/Vis Absorption spectrum of Brazzein was recorded on a Perkin-Elmer 559A UV-VIS spectrophotometer with 1 mg/ml Brazzein in water. The wavelength range is from 190 nm to 700 nm, and the scanning speed is 20 nm/min. The absorption exhibited confirmed that what we had isolated was a protein.

Thermostability Assays

A thermostability assay was done (2 hours at 98° C.) at a concentration of 0.5 mg/ml Brazzein at the following different pH levels: 2 (Glycine-HCL buffer); 4 (Acetate buffer); 6 (Phosphate buffer); and 8 (Tris-HCL buffer). All of the buffers were in concentration of 50 mM. After the incubations, the samples were cooled down to room temperature and the sweetness of the samples was tasted with a comparison to the original protein solution. The protein exhibited excellent thermostability.

Amino Acid Composition Analysis

A preliminary amino acid analysis was done by using the Pico-Tag system of Waters. The purified protein sample was hydrolyzed in 6N HCl under 110° C. for 24 hours first and the derivatization was done by using PITC according to the standard procedure. See S. A. Cohen et al., *The Pico-Tag®Method, A Manual Of Advanced Techniques For Amino Acid Analysis,* Millipore Co. (1989). The amino acid composition indicated a high incidence of lysine.

Protein Sequence Determination

The purified Brazzein was then sequenced on an ABI 470A Protein Sequencer. The sequence was obtained from 400 picomoles observed sample.

In our preferred experiment we dissolved the Brazzein in 8M urea, 0.4M $NH_4HCO_3$ with 5 mM dithiothreitol; incubated at 50° C. for 15 min; then added iodoacetamide to 10 mM after cooling to room temperature; and then incubated for another 15 min. Finally, we diluted the urea in whole reation system to 2M and added trypsin (TPCK treated) in ratio of 1 to 50 of Brazzein. We then incubated the reaction at 37° C. for 24 hours and stopped the reaction by injecting directly onto a reverse phase HPLC system. Trypsin-digested peptides were isolated by manual collection (see J. E. Shively, *"Reverse Phase HPLC Isolation and Microsequencing Analysis"* in *"Methods of Protein Microcharacterization,"* (Humana Press 1986).

SEQ ID NO:1 is the amino acid sequence we initially obtained for one sample of the protein. Subsequently, we resequenced the protein and obtained SEQ ID NO:4, which we believe is the preferred form of the protein.

Brazzein Sequence Analysis

In order to confirm the degree of uniqueness of Brazzein, BLAST and FASTA in the Gen Bank were used to carry out a homology search with SEQ ID NO:I. See S. F. Altschul et al., J. Mol. Biol. 215:403–410 (1990); W. R. Pearson et al., PNAS U.S.A. 85:2444–2448 (1988). NBRF/PIR V.31 and Swiss-Prot V.21 were used as searching databases. No significant sequence homology was found.

As indicated by SEQ ID NOs:1 and 4, nearly one seventh of the amino acid composition of Brazzein is lysine, an essential amino acid. Thus, not only does this sweetener have desirable heat stability and temporal characteristics, it is a possible source of lysine.

Note that Brazzein is so sweet that only a very small amount of it will be needed to sweeten coffee, tea, or the like. For such uses, it can be blended with a bulky filler (e.g. lactose) to give the user a feeling of perceived value.

Expression Of DNA

Originally, we had devised SEQ ID NOs:2 and 3 from the SEQ ID NO:1 amino acid sequence to express Brazzein. When we resequenced the Brazzein protein to obtain SEQ ID NO:4, we created SEQ ID NOs: 5 and 6 based thereon. SEQ ID NO:5 is a generic DNA sequence encoding Brazzein, prepared from a standard codon usage table. SEQ ID NO:6 was prepared from a codon usage table developed specifically for *E. coli.* SEQ ID NO:5 or 6 are preferably used with an ATG initiation codon.

If one desires to produce the sweetener artificially, one could synthesize a SEQ ID NO:5 sequence (such as SEQ ID NO:6) by combining standard cloning and an automated synthesizer techniques (e.g. 380 B ABI DNA synthesizer). The gene could then be cloned in one of the well known *E. coli* expression vectors such as pGEMEX®-1 (Promega), at the T7 gene 10 site (using conventional techniques). The vector could then be inserted in host JM109 (DE3) (Promega), with expression in the usual manner.

Brazzein could then be harvested as part of a fusion protein. If desired, modifications could be made in the usual way to reduce or eliminate underdesired portions of the fusion proteins.

We claim:

1. A sweet protein containing an amino acid sequence according to SEQ ID NO:4 amino acid residues 2–54, wherein the protein has been produced recombinantly and is essentially free of *Pentadiplandra brazzeana* plant material other than Brazzein.

2. A composition comprising the protein of claim 1 mixed with another sweetener obtained from other than *Pentadiplandra brazzeana* Baillon.

3. The composition of claim 2, wherein the other sweetener has a temporal profile which provides a faster sweetness response than Brazzein.

4. A DNA sequence according to SEQ ID NO:5 bases 4–162, wherein the DNA sequence is located outside of a *Pentadiplandra brazzeana* Baillon cell, and the DNA sequence encodes the protein of SEQ ID NO:4 residues 2–54, wherein the DNA sequence is essentially free of *Pentadiplandra brazzeana* plant material other than Brazzein.

5. An isolated and purified DNA sequence which encodes the protein of claim 1.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 52 amino acids

```
                    ( B ) TYPE: amino acid
                    ( D ) TOPOLOGY: linear ( i i ) MOLECULE TYPE: protein ( v i ) ORIGINAL SOURCE:
                    ( A ) ORGANISM: Pentadiplandra brazzeana
                    ( B ) STRAIN: Baillon ( x i ) SEQUENCE DESCRIPTION: SEQ ID NO:1:
```

| Asp | Lys | Cys | Lys | Lys | Val | Tyr | Glu | Asn | Tyr | Pro | Val | Ser | Lys | Cys | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ala | Asn | Gln | Cys | Asn | Tyr | Asp | Cys | Lys | Leu | Asp | Lys | His | Ala | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Gly | Glu | Cys | Phe | Tyr | Asp | Glu | Lys | Arg | Asn | Leu | Gln | Cys | Ile | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Tyr | Cys | Gly |
|-----|-----|-----|-----|
|     |     | 50  |     |

```
( 2 ) INFORMATION FOR SEQ ID NO:2:

( i ) SEQUENCE CHARACTERISTICS:
                    ( A ) LENGTH: 156 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:2:

GAYAARTGYA  ARAARGTNTA  YGARAAYTAY  CCNGTNWSNA  ARTGYCARYT  NGCNAAYCAR        60

TGYAAYTAYG  AYTGYAARYT  NGAYAARCAY  GCNMGNWSNG  GNGARTGYTT  YTAYGAYGAR       120

AARMGNAAYY  TNCARTGYAT  HGGNGAYTAY  TGYGGN                                    156

( 2 ) INFORMATION FOR SEQ ID NO:3:

( i ) SEQUENCE CHARACTERISTICS:
                    ( A ) LENGTH: 156 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:3:

GACAAATGCA  AAAAAGTTTA  CGAAAACTAC  CCGGTTTCCA  AATGCCAGCT  GGCTAACCAG        60

TGCAACTACG  ACTGCAAACT  GGACAAACAC  GCTCGTTCCG  GTGAATGCTT  CTACGACGAA       120

AAACGTAACC  TGCAGTGCAT  CGGTGACTAC  TGCGGT                                    156

( 2 ) INFORMATION FOR SEQ ID NO:4:

( i ) SEQUENCE CHARACTERISTICS:
                    ( A ) LENGTH: 54 amino acids
                    ( B ) TYPE: amino acid
                    ( D ) TOPOLOGY: linear ( i i ) MOLECULE TYPE: protein ( i x ) FEATURE:
```

(A) NAME/KEY: Modified-site
(B) LOCATION: 1
(D) OTHER INFORMATION: /label=Pyroglutamate
/ note="N-terminal amino acid is a modified glutamic acid residue."

(xi) SEQUENCE DESCRIPTION: SEQ ID NO:4:

| Glu | Asp | Lys | Cys | Lys | Lys | Val | Tyr | Glu | Asn | Tyr | Pro | Val | Ser | Lys | Cys |
|---|---|---|---|---|---|---|---|---|---|---|---|---|---|---|---|
| 1 | | | | 5 | | | | | 10 | | | | | 15 | |

| Gln | Leu | Ala | Asn | Gln | Cys | Asn | Tyr | Asp | Cys | Lys | Leu | Asp | Lys | His | Ala |
|---|---|---|---|---|---|---|---|---|---|---|---|---|---|---|---|
| | | | 20 | | | | | 25 | | | | | 30 | | |

| Arg | Ser | Gly | Glu | Cys | Phe | Tyr | Asp | Glu | Lys | Arg | Asn | Leu | Gln | Cys | Ile |
|---|---|---|---|---|---|---|---|---|---|---|---|---|---|---|---|
| | | 35 | | | | | 40 | | | | | 45 | | | |

| Cys | Asp | Tyr | Cys | Glu | Tyr |
|---|---|---|---|---|---|
| | 50 | | | | |

(2) INFORMATION FOR SEQ ID NO:5:

(i) SEQUENCE CHARACTERISTICS:
(A) LENGTH: 162 base pairs
(B) TYPE: nucleic acid
(C) STRANDEDNESS: double
(D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:5:

```
CARGAYAART GYAARAARGT NTAYGARAAY TAYCCNGTNW SNAARTGYCA RYTNGCNAAY     60
CARTGYAAYT AYGAYTGYAA RYTNGAYAAR CAYGCNMGNW SNGGNGARTG YTTTYTAYGAY  120
GARAARMGNA AYYTNCARTG YATHTGYGAY TAYTGYGART AY                      162
```

(2) INFORMATION FOR SEQ ID NO:6:

(i) SEQUENCE CHARACTERISTICS:
(A) LENGTH: 162 base pairs
(B) TYPE: nucleic acid
(C) STRANDEDNESS: double
(D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:6:

```
CAGGACAAAT GTAAAAAAGT ATACGAAAAC TACCCGGTAT CCAAATGTCA GCTGGCAAAC     60
CAGTGTAACT ACGACTGTAA ACTGGACAAA CACGCTCGTT CCGGTGAATG CTTCTACGAC   120
GAAAAACGTA ACCTGCAGTG CATCTGCGAC TACTGCGAAT AC                      162
```